(12) United States Patent
Leona et al.

(10) Patent No.: US 7,787,117 B1
(45) Date of Patent: Aug. 31, 2010

(54) METHOD AND APPARATUS FOR IN SITU MEASUREMENT OF MATERIAL PROPERTIES BY SURFACE ENHANCED RAMAN SPECTROSCOPY

(75) Inventors: Marco Leona, New York, NY (US); Thomas J. Tague, Jr., Richmond, NH (US)

(73) Assignee: Bruker Optics, Inc., Billerica, MA (US)

( * ) Notice: Subject to any disclaimer, the term of this patent is extended or adjusted under 35 U.S.C. 154(b) by 164 days.

(21) Appl. No.: 12/145,018

(22) Filed: Jun. 24, 2008

(51) Int. Cl.
*G01J 3/44* (2006.01)
*G01N 21/65* (2006.01)

(52) U.S. Cl. .................................................. 356/301

(58) Field of Classification Search .................. 356/301, 356/36
See application file for complete search history.

(56) References Cited

U.S. PATENT DOCUMENTS

| | | | |
|---|---|---|---|
| 6,850,323 B2 * | 2/2005 | Anderson | 356/301 |
| 7,248,360 B2 | 7/2007 | Horchner et al. | |
| 2005/0250159 A1 | 11/2005 | Su et al. | |
| 2007/0035729 A1 | 2/2007 | Leona | |
| 2008/0305489 A1 | 12/2008 | Thomas et al. | |
| 2009/0053818 A1 | 2/2009 | Zhang et al. | |

FOREIGN PATENT DOCUMENTS

WO   WO 2006037036 A2   4/2006

OTHER PUBLICATIONS

Canamares, et al., "Surface-Enhanced Raman Scattering Study of the Adsorption of the Anthraquinone Pigment Alizarin on Ag Nanoparticles", J. of Raman Spectrosc., 2004; 35:921-927, 2004, John Wiley & Sons, Ltd.
Chen, et al., "Application of Surface-Enhanced Raman Scattering (SERS) for the Identification of Anthraquinone Dyes Used in Works of Art", J. of Raman Spectrosc., 2006; 37:520-527, 2006, John Wiley & Sons, Ltd.
Etchegoin, et al., "Electromagnetic Contribution to Surface Enhanced Raman Scattering Revisited", J. of Chem. Phys., vol. 119, No. 10, Sep. 8, 2003.
Leona, et al., "Application of Surface-Enhanced Raman Scattering Techniques to the Ultrasensitive Identification of Natural Dyes in Works of Art", J. of Raman Spectrosc., 2006; 37:981-992, 2006, John Wiley & Sons, Ltd.
Leona, "Surface-Enhanced Raman Scattering in Art and Archaeology", Proc. SPIE, vol. 5993, 2005.
Leona, "Sub-Nanogram Level Identification of Alizarin by Surface Enhanced Raman Scattering", Proc. Volume of the Sixth Infrared and Raman Users Group Conference (IRUG6), Florence, Italy, 2004.

(Continued)

*Primary Examiner*—F. L Evans
(74) *Attorney, Agent, or Firm*—Law Offices of Paul E. Kudirka

(57) ABSTRACT

In apparatus for performing Surface Enhanced Raman Spectroscopy (SERS), rather than applying a sample to be analyzed to an SERS active substrate, the SERS active substrate is applied to the sample using an inkjet nozzle to apply a substance containing a colloidal metal, such as silver, to the sample. The prepared sample is then analyzed with a Raman spectrometer in a conventional fashion.

22 Claims, 2 Drawing Sheets

OTHER PUBLICATIONS

Leona, "Identification of Berberine in Ancient and Historical Textiles by Surface-Enhanced Raman Scattering", J. of Raman Spectrosc., 2007; 38:853-858, John Wiley & Sons, Ltd.

Teslova, "Raman and Surface-Enhanced Raman Spectra of Flavone and Several Hydroxy Derivative," J. of Raman Spectrosc., 2007, pp. 1-17, John Wiley & Sons, Ltd.

Wang, "Raman and Surface Enhanced Raman Scattering of 3-Hydroxyflavone", J. Phys. Chem., C 2007, 111, 3038-3043.

Moskovits, "Surface-Enhanced Raman Spectroscopy: A Brief Retropective", J. of Raman Spectrosc., 2005; 36:485-496, John Wiley & Sons, Ltd. (Abstract Only).

* cited by examiner

FIG. 1 *(Prior Art)*

METHOD AND APPARATUS FOR IN SITU MEASUREMENT OF MATERIAL PROPERTIES BY SURFACE ENHANCED RAMAN SPECTROSCOPY

BACKGROUND

Raman spectroscopy is a spectroscopic technique used to study vibrational, rotational, and other low-frequency modes of materials. The technique relies on inelastic scattering of monochromatic light in the visible, near infrared, or near ultraviolet range. The light interacts with phonons or other excitations in the material, resulting in a shift in the energy of the light photons from which shift information about the phonon modes in the system can be derived. A Raman spectrum contains many different peaks. Each peak corresponds to the energy of the vibration of a chemical bond in the molecule. Therefore, a Raman spectrum can be nearly a unique fingerprint of a molecule. The spectrum can be used, for example, in analytical chemistry to identify the various molecules in an unknown sample.

Typically, in a conventional Raman spectroscopy set up, such as that shown in FIG. 1, a sample 106 is illuminated with a laser beam 102. The laser beam 102 is generated by a laser 100, deflected via a semi-transparent or dichroic mirror 108 through an objective lens 104 onto the sample 106. The radiation which is scattered back from the sample surface 106 travels through the lens 104 in the opposite direction and passes through the semi-transparent mirror 108. The scattered light then passes through other parts of the spectrometer, which are not shown in the drawing, where wavelengths close to the laser line, produced by elastic Rayleigh scattering, are filtered out. The remainder of the collected scattered light is dispersed onto a detector 110.

Conventional Raman spectroscopy is an ideal tool for non-destructive in-situ investigations and is characterized by both its very high spectral resolution, which permits effective discrimination among various species, and by its high spatial resolution (when a microscope is used). Because the inelastic Raman scattering is relatively weak, Raman spectrometers typically use holographic diffraction gratings and multiple dispersion stages to achieve a high degree of rejection of the laser light. However, even with these refinements, the low intensity of normal Raman scattering and the tendency of many analytes to fluoresce under laser excitation have prevented wider application of the technique as a sensitive spectroscopic probe.

In an enhanced Raman technique called Surface Enhanced Raman Spectroscopy (SERS), the weak Raman scattering intensity is greatly strengthened (by a factor of many orders of magnitude as compared to the intensity obtained from the same number of molecules in solution or in the gas phase) by either attaching the molecules which produce the inelastic scattering to metal structures of nanoscale size or locating the metal structures in the vicinity of the molecules. The exact mechanism involved has not been determined at the present time, but the SERS effect has been observed for molecular species adsorbed on rough metal surfaces. See, for example, "Surface Enhanced Raman Scattering", Chang, R. K.; Furtak, T. E., Plenum, New York, (1982); "Surface Enhanced Raman Scattering; Chemical and Biochemical Applications of Lasers", Van Duyne, R. P., edited by C. B. Moore, v. 4, p. 101, Academic Press, New York, (1979); "Surface Enhanced Spectroscopy", Moskovits, M., *Review of Modern Physics*, v. 57, p. 783 (1985); "Surface Enhanced Raman Scattering; in Spectroelectrochemistry: Theory and Practice", Birke, R. L., Lombardi, J. R., edited by R. J. Gale, Plenum, (1988). At the same time, the proximity of the molecular species to the surface of the substrate provides a non-radiative pathway for relaxation from the excited states of the molecules, which successfully quenches fluorescence.

The SERS technique can be used to conduct Raman spectroscopy studies of analytes, such as pharmaceutical compounds, and other organic substances that are too fluorescent, or are present in very minute concentrations in their matrices to yield usable Raman spectra. One area of particular interest is the applicability of SERS to natural and synthetic dyes which has great importance in the museum field in support of art historical, archaeological, and anthropological studies, and to evaluate susceptibility of artistic works to light induced fading.

Organic substances have been used for millennia as textile dyes or, complexed with metal ions, as pigments for artistic or utilitarian objects. Anthraquinones such as alizarin and purpurin (from the root of *rubia tinctorum* L.), carminic acid (from the insect *Dactylopius coccus* C.), the laccaic acids (from the insect *Kerria lacca* K.), or naphtoquinones such as lawsone and juglone, neoflavonoids such as brazilein, flavonoids such as quercetin and morin, and the alkaloid berberine, are found in works of art as red, purple, brown, and yellow dyes. These molecules are also found in modern products: carminic acid is a common red dye for beverages and cosmetics. Beyond the arts field, the molecules are all relevant to other fields, either directly or as proxies for other compounds: in pharmaceutical studies (berberine, anthraquinoid anticancer drugs), in the forensic field (in evidence such as lipsticks, inks, drugs of abuse, toxic agents), in the food colorants industry, and in the textile dyeing industry.

The identification of dyes is generally conducted by extraction followed by high performance liquid chromatography analysis. This analysis requires a sizable sample (5 millimeter of threads from a textile, for instance) and makes it impossible to analyze paintings and drawings, where samples larger than 100 μm cannot be removed. However, SERS has been successfully applied to the identification of synthetic anthraquinones, an SERS method has been developed for the extraction and identification of alizarin at sub-nanogram levels in paint samples and positive results have been obtained for highly fluorescent molecules, such as alizarin, purpurin, laccaic acid, carminic acid, kermesic acid, shikonin, juglone, lawsone, brazilin and brazilein, haematoxylin and haematein, fisetin, quercitrin, quercetin, rutin, morin, and berberine.

One prior art technique allows the spectra of natural dyes to be obtained from actual textile samples and directly from extremely small samples (1 mm×25 μm) of dyed fibers with SERS active substrates including Ag colloids obtained by reduction with sodium citrate or with hydroxylamine hydrochloride, silver films obtained by chemical deposition with the Tollens reaction, and silver nanoislands films obtained by vacuum evaporation.

However, it would be desirable to be able to analyze even smaller samples and, particularly, to be able to selectively analyze portions of small samples.

SUMMARY

In accordance with the principles of the invention, rather than delivering the sample to an SERS active substrate, the SERS substrate is applied to the sample. In particular, inkjet technology is used to apply a colloidal substance to the sample to form an SERS substrate in a more controlled and spatially circumscribed fashion when compared to other SERS techniques. By limiting the volume of colloid delivered to the sample, the sensitivity of SERS detection can be enhanced by avoiding dilution of the analyte. Further, spatial specificity is also enhanced, since nanoparticle probes can be accurately delivered to a specific part of the object under analysis.

In one embodiment, a thermal inkjet nozzle is used to deliver a colloid to the sample surface.

In another embodiment, a piezoelectric inkjet nozzle is used to deliver the colloid to the sample surface.

In yet another embodiment, a colloidal substance is applied to the sample surface followed by the application of an aggregating agent.

In still another embodiment, the colloidal substance and the aggregating agent are mixed together and the mixture is applied to the sample surface.

DETAILED DESCRIPTION

Figure 1:
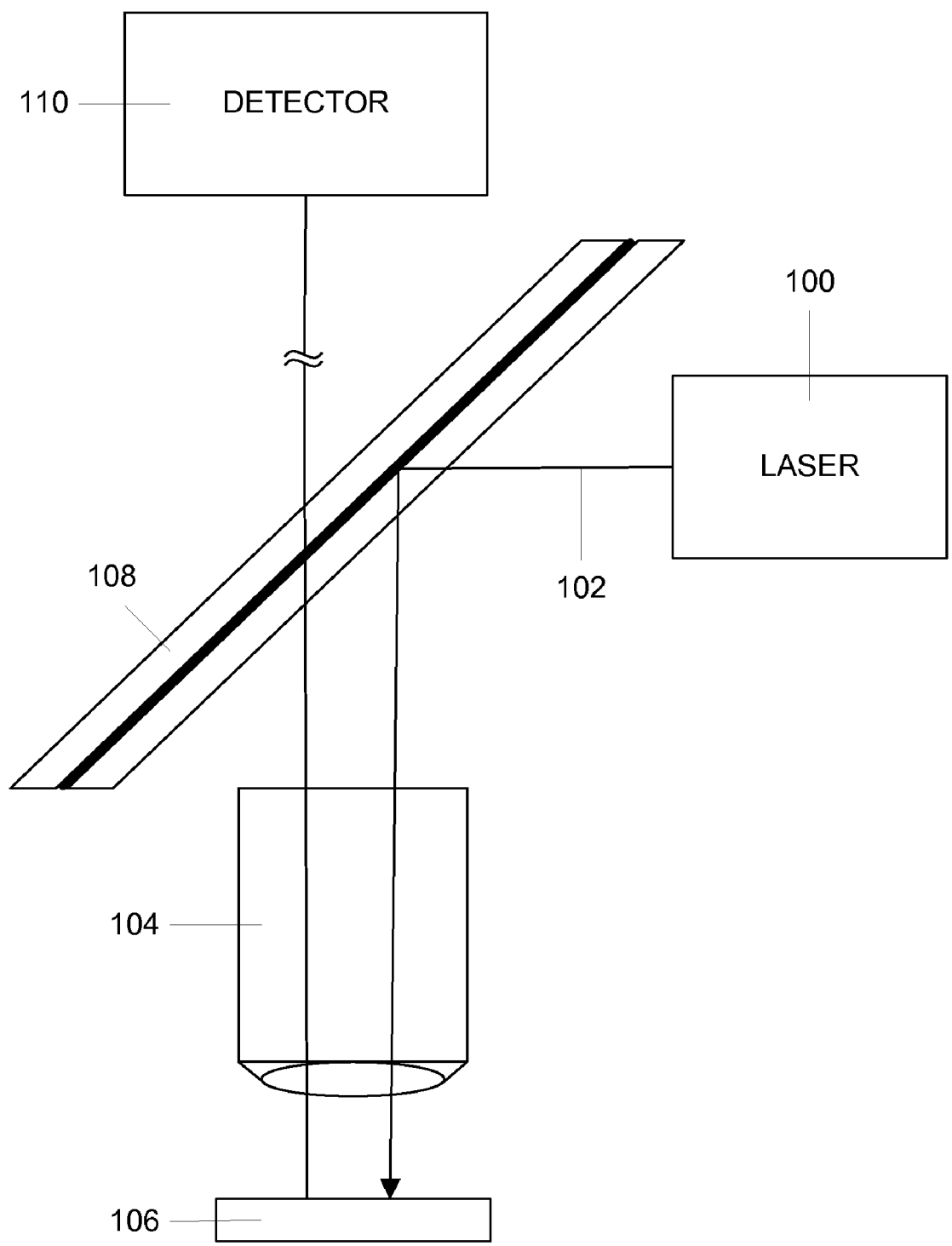
FIG. 1 is a block schematic diagram of the optical path in a conventional Raman microscope.
Figure 2:
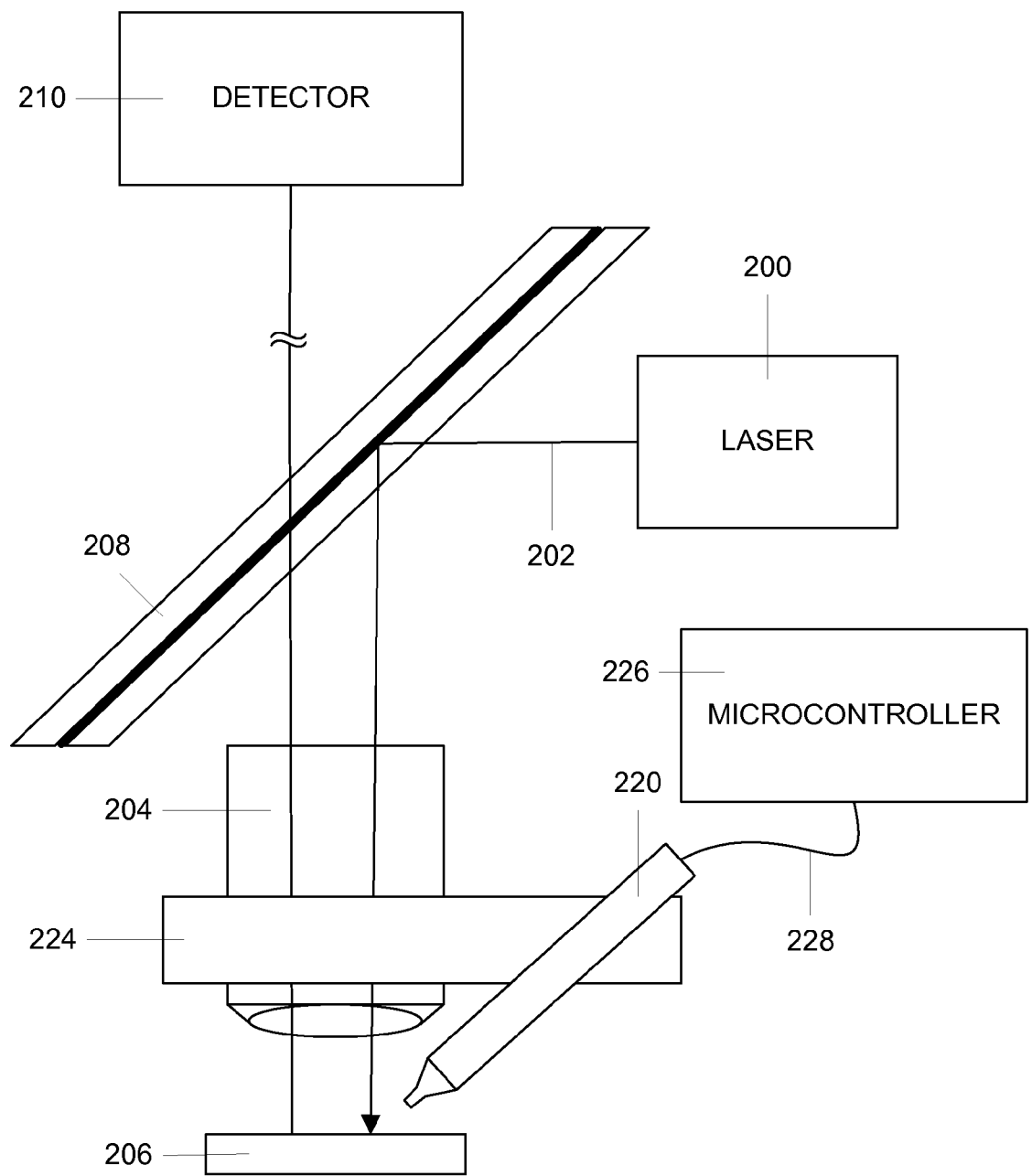
FIG. 2 is a block schematic diagram of the optical path in a Raman microscope incorporating an inkjet nozzle for applying an SERS substrate to a sample.

An embodiment of the invention is shown in FIG. 2 as an accessory for a Raman microscope. As shown in FIG. 2, the optical path of the enhanced microscope is the same as the conventional optical path. In FIG. 2, elements that correspond to elements in FIG. 1 have been given corresponding numeral designations. For example laser 200 in FIG. 2 corresponds to laser 100 in FIG. 1. An inkjet nozzle 220 is attached to the microscope objective 104 by means of a bracket 224.

A Raman microscope that is satisfactory for use with the invention is a Senterra model developed and sold by Bruker Optics, Inc. 19 Fortune Drive, Billerica, Mass. The inkjet nozzle 220 can be any of several convention elements available. One nano-dispensing system suitable for use with the invention is a Hewlett Packard HP51604A inkjet cartridge (a 96 dpi, 12-nozzle thermal printhead) wherein one nozzle is controlled by a Basic Stamp microcontroller 226 as shown schematically by lead 228.

The inkjet nozzle 220 applies a colloid to the surface of sample 206. One suitable colloid is a silver (Ag) colloid prepared either by reduction with sodium citrate or by reduction with hydroxylamine hydrochloride. In both cases, all glassware was cleaned following a conventional procedure and only ultrapure water was used for the preparation of the various solutions. Citrate reduced colloids were prepared following the procedure described in detail in "Adsorption and surface-enhanced Raman of dyes on silver and gold sols", Lee, P. C., and Meisel, D., *Journal of Physical Chemistry* v. 86, pp 3391-3395 (1982) by reduction of silver nitrate (Aldrich 209139 Silver Nitrate 99.9%) with sodium citrate (Aldrich W302600 Sodium Citrate Dihydrate). The colloid thus prepared shows an absorption maximum at 406 nm and FWHM of 106 nm, as measured with a Cary 50 UV-Vis Spectrophotometer (after a 1:4 dilution with ultrapure water to keep maximum absorbance within the instrumental range). To further concentrate the colloid for use, a volume of 10 ml of the original colloid was centrifuged at 5000 rpm. The supernatant was discarded and the settled portion was resuspended in 1 ml of ultrapure water.

Hydroxylamine hydrochloride reduced Ag colloids were prepared following the method described in detail in Leopold N, Lendl B. *Journal of Physical Chemistry B*, v. 107, p5723 (2003) and concentrated for use by centrifugation.

Each nozzle in the aforementioned inkjet head is capable of depositing drops of Ag colloid of approximately 200-300 micrometers on a sample. In one experiment, SERS spectra were successfully obtained from Ag dots deposited on berberine or alizarin impregnated filter paper, with or without inkjet deposition of appropriate aggregating agents, such as $KNO_3$ or poly-L-lysine. In another embodiment, it was found that pre-aggregated colloids (obtained by pre-mixing Ag colloid and an aggregating agent) could be deposited using the thermal inkjet nozzle without clogging the inkjet nozzle (approximately 150 micrometer diameter).

Using this arrangement, extremely small samples from artifacts (fibers, documents, trace evidence) can be analyzed since all of the phases of the SERS protocol can be integrated on the microscope, including sample localization, SERS probe deposition, and Raman analysis.

In other embodiments, the deposition parameters, including the droplet ejection velocity, can be optimized by controlling the pulse width and shape using the microcontroller to result in penetration of the colloid inside biological material, with possible applications to cell penetration or tissue section studies.

The technique can be used to deposit SERS materials on the surface of microscopic samples such as textile or paper fibers, or on whole objects such as documents, drug pills, and trace evidence in situ (such as fingerprints, lipstick stains, etc.). Additionally, the technique can be used to analyze tissue sections for localization of biologically active or pharmaceutical compounds, and to deliver SERS materials to cells or other biological materials. High droplet velocity ejection can be used to insert the SERS material into cells or living tissue prior to SERS analysis.

Although a thermal inkjet nozzle is described above, it is also possible to use an inkjet nozzle in a piezoelectric inkjet head, such as an MJ-AT-01 Minstac piezoelectric inkjet head from Microfab Technologies, Inc. with small nozzle diameter (50 micrometer). As with the thermal inkjet head, the piezoelectric head can be controlled with a dedicated controller to change pulse parameters to modify factors such as droplet ejection velocity and to optimize droplet volume. The piezoelectric system may be used to deliver SERS substrates other than Ag colloids, namely, suspensions of Ag coated microspheres, nanoparticles, and carbon nanotubes.

While the invention has been shown and described with reference to a number of embodiments thereof, it will be recognized by those skilled in the art that various changes in form and detail may be made herein without departing from the spirit and scope of the invention as defined by the appended claims.

What is claimed is:

1. Apparatus for in situ measurement of properties of a sample surface by Surface Enhanced Raman Spectroscopy (SERS), comprising:
    a device that applies droplets of a SERS active liquid material onto the sample surface; and a Raman spectrometer that measures Raman radiation scattered from the SERS active material.

2. The apparatus of claim 1 wherein the device can deliver onto the sample surface droplets of the SERS active material having a diameter in the range of 25-75 micrometers.

3. The apparatus of claim 1 wherein the device is an inkjet nozzle.

4. The apparatus of claim 3 wherein the inkjet nozzle is a thermal inkjet nozzle.

5. The apparatus of claim 3 wherein the inkjet nozzle is a piezoelectric inkjet nozzle.

6. The apparatus of claim 1 wherein the Raman spectrometer has a Raman microscope with a microscope objective lens and wherein the device is affixed to the microscope objective lens.

7. The apparatus of claim 1 wherein the SERS active material comprises a material selected from the group consisting of silver colloids, gold colloids, copper colloids, metal coated nanospheres, metal-coated nanoparticles, and carbon nanotubes.

8. The apparatus of claim 7 wherein the SERS active material further comprises an aggregating agent.

9. The apparatus of claim 1 further comprising a controller for controlling parameters of the device that affect a manner in which the SERS active material is applied to the sample surface.

10. The apparatus of claim 9 wherein the device is an inkjet nozzle and the parameters affect an amount of the SERS active material which is applied to the sample surface.

11. The apparatus of claim 9 wherein the device is an inkjet nozzle and the parameters affect a velocity at which the SERS active material is applied to the sample surface.

12. The apparatus of claim 9 wherein the control controls the device to apply an SERS active material followed by an aggregating agent.

13. A method for in situ measurement of properties of a sample surface by Surface Enhanced Raman Spectroscopy (SERS), comprising:
    (a) applying droplets of a SERS active liquid material onto the sample surface; and
    (b) measuring Raman radiation scattered from the SERS active material.

14. The method of claim 13 wherein step (a) comprises delivering onto the sample surface droplets of the SERS active material having a diameter in the range of 25-75 micrometers.

15. The method of claim 13 wherein step (a) comprises applying a SERS active material onto the sample surface with an inkjet nozzle.

16. The method of claim 15 wherein the inkjet nozzle is a thermal inkjet nozzle.

17. The method of claim 15 wherein the inkjet nozzle is a piezoelectric inkjet nozzle.

18. The method of claim 13 wherein the SERS active material comprises a material selected from the group consisting of silver colloids, gold colloids, copper colloids, metal coated nanospheres, metal-coated nanoparticles, and carbon nanotubes.

19. The method of claim 18 wherein the SERS active material further comprises an aggregating agent so that the SERS active material and the aggregating agent are applied simultaneously in step (a).

20. The method of claim 13 wherein the device is an inkjet nozzle and wherein step (a) comprises controlling parameters of the inkjet nozzle that affect an amount of the SERS active material which is applied to the sample surface.

21. The method of claim 13 wherein the device is an inkjet nozzle and wherein step (a) comprises controlling parameters of the inkjet nozzle that affect a velocity at which the SERS active material is applied to the sample surface.

22. The method of claim 13 wherein step (a) comprises applying an SERS active material to the sample surface followed by applying an aggregating agent to the sample surface.

\* \* \* \* \*